United States Patent [19]

Husson et al.

[11] Patent Number: 5,310,739

[45] Date of Patent: May 10, 1994

[54] 1-AMIDOOCTAHYDROPYRIDO[2,1-C][1,4]OXAZINE COMPOUNDS

[75] Inventors: Henri P. Husson, Chevreuse; Jean C. Quirion; Martine Bonin, both of Gif sur Yvette; Béatrice Guardiola, Neuilly sur Seine; Gérard Adam, Le Mesnil le Roi; Pierre Renard, Versailles, all of France

[73] Assignee: Adir et Compagnie, Courbevoie, France

[21] Appl. No.: 882,273

[22] Filed: May 13, 1992

[30] Foreign Application Priority Data

May 14, 1991 [FR] France ................. 91 05765

[51] Int. Cl.$^5$ ............... A61K 31/535; C07D 498/04
[52] U.S. Cl. ................. 514/230.5; 544/100; 544/105
[58] Field of Search ............ 544/105; 514/230.5

[56] References Cited

U.S. PATENT DOCUMENTS 4,346,089 8/1982 Hadley et al. ............... 544/105

FOREIGN PATENT DOCUMENTS 57536 8/1982 European Pat. Off. ........... 544/105

OTHER PUBLICATIONS

*Drug Evaluations*, 6th Ed (1986), American Medical Association, pp. 111–117.

Puech, et al., Psychopharmacology 75, 84–91 (1981).
Chermat, et al., J. Pharmacol 17, 348–350 (1986).
Stéru, et al., Prog. Neuro-Psychopharmacol. & Biol. Psychiat. 11, 659–671 (1987).

*Primary Examiner*—Mukund J. Shah
*Assistant Examiner*—Philip Datlow
*Attorney, Agent, or Firm*—Gordon W. Hueschen

[57] ABSTRACT

The invention relates to the compounds of general formula

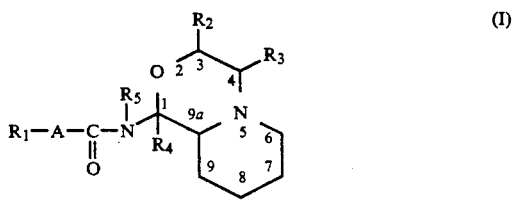

in which $R_1$, $R_2$, $R_4$, $R_5$ and A are as defined in the description.

their isomers, diastereoisomers, and enantiomers as well as their addition salts with a pharmaceutically acceptable inorganic or organic acid, and medicinal products containing the same which are usable for the treatment of psycho-behavioral disorders.

10 Claims, No Drawings

1-AMIDOOCTAHYDROPYRIDO[2,1-C][1,4]OXAZINE COMPOUNDS

The invention relates to new 1-amidooctahydropyrido[2,1-c][1,4]oxazine compounds, to a process for preparing these and to pharmaceutical compositions containing them.

Benzamide compounds obtained from 9-aminooctahydropyrido[2,1-c][1,4]oxazines (patent EP 57,536 A1 820811) and from 8-aminooctahydropyrido[2,1-c][1,4]oxazines (patent EP 34,015 A2 810819) are already known for their capacity to improve the motility of the gastrointestinal tract.

The Applicant's compounds possess a completely novel 1-aminooctahydropyrido[2,1-c][1,4]oxazine structure capable of being obtained stereospecifically, and some of them are endowed with noteworthy psychotropic properties, being strongly antidepressant, antipsychotic, neuroleptic.

More specifically, the invention relates to the 1-acylaminooctahydropyrido[2,1-c][1,4]oxazines of general formula (I):

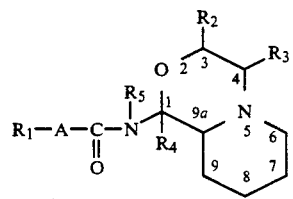

in which:
- $R_1$ represents a hydrogen or an optionally substituted mono- or bicyclic system chosen from phenyl, naphthyl, pyridyl, thienyl, furyl, quinolyl, isoquinolyl, indolyl, indolinyl, perhydroindolyl, benzofuryl,
- A represents a bond or a saturated or unsaturated, linear or branched alkylene having 1 to 4 carbon atoms, with the reservation that when $R_1$ represents a hydrogen, A cannot represent a σ bond,
- $R_2$ and $R_3$ each represent, independently of one another
  - a hydrogen,
  - a linear or branched and optionally substituted alkyl having 1 to 6 carbon atoms,
  - a group —$(CH_2)_nB$, with n being able to take the values 0, 1, 2, 3 and B representing a saturated, unsaturated or aromatic 5- to 7-membered monocyclic system, substituted or otherwise,
  - or $R_2$ and $R_3$, together with the carbon atoms to which they are linked, form an optionally substituted 5- to 7-membered saturated cyclic system,
- $R_4$ and $R_5$ each represent, independently of one another, a hydrogen, a linear or branched alkyl having 1 to 4 carbon atoms or a group —$(CH_2)_nB$ as defined in the description of $R_2$ and $R_3$, the term substituted associated with the expression "mono- or bicyclic system" means that these ring- systems may be substituted with one or more (maximum 4) lower alkyl groups having 1 to 4 carbon atoms, branched or otherwise, nitro or amino groups, lower alkoxy groups having 1 to 4 carbon atoms, branched or otherwise, hydroxyl, trifluoromethyl or halogen groups or groups $SO_2R_6$, it being possible for these substituted groups to be identical or different, the term substituted associated with the expression alkyl means that this group may be substituted with one or more linear or branched lower alkoxy groups having 1 to 4 carbon atoms, $R_6$ represents a lower alkyl having 1 to 4 carbon atoms, branched or otherwise, a phenyl (optionally substituted with one or more linear or branched lower alkyl or alkoxy groups having 1 to 4 carbon atoms or trifluoromethyl or halogen groups) or a group —$NR_7R_8$ in which $R_7$ and $R_8$ can represent, independently of one another, a hydrogen or a lower alkyl having 1 to 4 carbon atoms, branched or otherwise, their isomers, diastereoisomers and enantiomers, isolated or in the form of a mixture, their addition salts with a pharmaceutically acceptable inorganic or organic acid.

The invention also encompasses the processes for obtaining the compounds of the general formula (I), wherein an amino alcohol of general formula (II):

in which $R_2$ and $R_3$ have the same meaning as in the compounds 10 of general formula (I), is reacted in an aqueous medium, in the presence of a weak acid and at a temperature of between 0° and 20° C., with glutaraldehyde and then, with or without intermediate isolation, with potassium cyanide at a temperature of between 10° C. and 30° C., so as to obtain, after isolation and purification by conventional techniques such as chromatography on a silica column and/or recrystallization, a bicyclic compound of general formula (III):

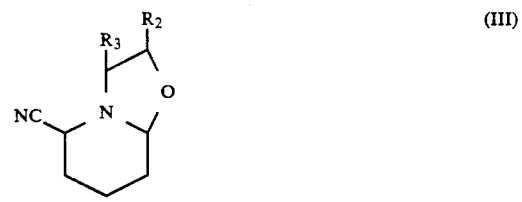

in which $R_2$ and $R_3$ have the same meaning as in the compounds of general formula (I), which can optionally be reacted, in an aprotic medium and at a temperature between −78° C. and room temperature, with an organolithium compound of general formula (IV):

in which $R'_4$ has the same definition as $R_4$ in the compounds of general formula (I), with the reservation that $R'_4$ cannot represent a hydrogen atom, so as to obtain an imine of general formula (V):

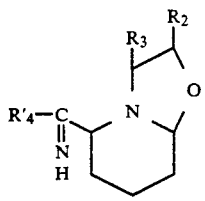

in which $R_2$ and $R_3$ have the same meaning as in the compounds of general formula (I) and $R'_4$ has the same meaning as in the compounds of general formula (IV), which may be reacted, like the nitriles of general formula (III), with a metal hydride in an aprotic medium, so as to obtain, after purification by conventional techniques such as chromatography on a silica column and/or recrystallization, a compound of general formula (VI):

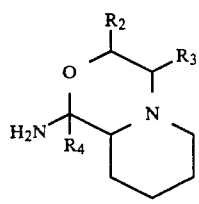

in which $R_2$, $R_3$ and $R_4$ have the same meaning as in the compounds of general formula (I) (the configuration of the asymmetric carbons of the compounds of general formulae (III) and (V) giving rise to the configuration of the asymmetric carbons of the compounds of general formula (VI)), which may be reacted:
either with a halogenated compound of general formula (VII):

in which $R_5$ has the same meaning as in the compounds of general formula (I) and X represents a halogen atom, so as to obtain, after isolation and, where appropriate, purification by conventional techniques such as chromatography on a silica column and/or recrystallization, a compound of general formula (VIII):

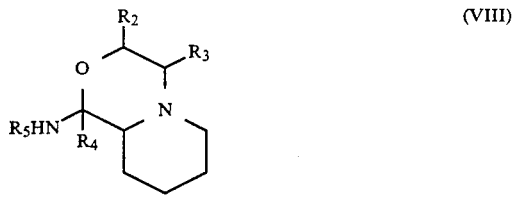

in which $R_2$, $R_3$, $R_4$ and $R_5$ have the same meaning as in the compounds of general formula (I), which is then reacted, optionally in the presence of a base, with an acid chloride of general formula (IX):

in which $R_1$ and A have the same meaning as in the compounds of general formula (I), so as to obtain, after isolation and purification by conventional techniques such as chromatography on a silica column and/or recrystallization, the compounds of general formula (I) for which $R_5$ does not represent a hydrogen atom, or directly with an acid chloride of general formula (IX), so as to obtain, after isolation and purification by conventional techniques such as chromatography on a silica column and/or recrystallization, the compounds of general formula (I) for which $R_5$ is a hydrogen atom which may then be N-alkylated according to conventional techniques with a compound of general formula (VII), so as to obtain the compounds of general formula (I) for which $R_5$ does not represent a hydrogen atom.

The compound of general formula (I) obtained by the methods mentioned above can, is so desired, be separated, if necessary, into their isomers and/or salified with a pharmaceutically acceptable acid.

The amides of the 1-aminooctahydropyrido[2,1-c][1,4]oxazines according to the present invention, as well as their addition salts with a pharmaceutically acceptable inorganic or organic acid, are very advantageous active principles for the treatment of psycho-behavioral disorders, and which may be used, inter alia, in the treatment of depressive states and psychoses.

The compounds of general formula (I), as well as their addition salts with a pharmaceutically acceptable inorganic or organic acid such as, for example, hydrochloric, methanesulfonic, nitric and maleic acids, may be presented in the form of pharmaceutical compositions according to known processes, such as, for example, in the form of tablets, capsules, dragées, injections, solutions or suspensions to be taken orally, emulsions and suppositories.

Apart from inert, non-toxic and pharmaceutically acceptable excipients such as, for example, distilled water, glucose, lactose, starch, talc, vegetables oils, ethylene glycol, and the like, these compositions can also contain preservatives.

The pharmaceutical compositions thereby obtained, which also form part of the invention, can contain, depending on the ailments being treated and the patient's age and weight, from 1 to 500 mg of active principle.

The examples which follow illustrate the invention and do not limit it in any way.

EXAMPLE 1

N-[(1R,4R,9aS)-4-phenyloctahydropyrido[2,1-c)(1,4]oxazin-1-yl]-3,4,5-trimethoxybenzamide

Stage I (2R)-2-amino-2-phenylethanol

A reactor under a nitrogen atmosphere is charged with 2.5 liters of anhydrous THF and then, in small portions, with 38 g (1 mol) of lithium aluminum hydride.

The suspension is heated to 60° C. and 100 g (0.66 mol) of (−)-(2R)-2-phenylglycine are then added in small portions. The reaction medium is then kept refluxing for 2 h 30 min and thereafter cooled to 5° C.

The excess hydride is destroyed by the dropwise addition of 38 cm³ of 15% aqueous sodium hydroxide solution, and finally 76 cm³ of water.

The salts are removed by filtration and washed 3 times with 200 cm³ of THF, and the combined filtrates are then concentrated under reduced pressure.

The orange-colored solid obtained is dried under vacuum, washed with ethyl ether and then recrystallized in toluene.

72.6 g (80%) of (2R)-2-amino-2-phenylethanol are thereby obtained in the form of white crystals.

Melting point: 78° C.

Optical rotation: $[\alpha]_D^{20} = -26,5°$ (CH$_3$OH, C = 0,7)

Stage II (3R,5S,8aR)-3-phenyl-5-cyanooxazolidino[3,2-a]piperidine

A reactor is charged with 1 liter of water and then 10 g (0.073 mol) of (2R)-2-amino-2-phenylethanol and 40 g (0.208 mol) of citric acid. The mixture is stirred until dissolution has taken place and then cooled to 0.5° C., and 45 cm$^3$ (0.11 mol) of an aqueous solution of glutaraldehyde are added dropwise in the course of 20 minutes. The mixture is stirred for 30 minutes at 0° C., cooling is then stopped and a solution of 7.15 g (0.11 mol) of potassium cyanide in 20 cm$^3$ of water and also 200 cm$^3$ of methylene chloride are added.

The two-phase reaction medium is stirred for 3 hours at room temperature and the aqueous phase is then neutralized by adding sodium bicarbonate.

After separation when settling has taken place, the aqueous phase is extracted with methylene chloride, and the combined methylene chloride phases are dried over sodium sulfate and concentrated under a partial vacuum to a residual volume of 0.5 liter.

2 g of zinc bromide are then added and the mixture is stirred vigorously under a nitrogen atmosphere for 3 hours (care should be taken regarding the possible release of hydrogen cyanide). The reaction medium is then concentrated to a residual volume of approximately 150 cm$^3$ and thereafter purified by chromatography on a silica column with a 2:1 hexane/ethyl ether mixture as eluant. The product obtained is finally recrystallized in hexane.

13.9 g (83 %) of (3R,5S,8aR)-3-phenyl-5-cyanooxazolidino[3,2-a]piperidine are thereby obtained.

Melting point: 81° C.

Optical rotation: $[\alpha]_D^{20} = -280°$ (CHCl$_3$, C = 1,0)

$^1$H NMR 400 MHz (CDCl$_3$) δ : ppm 1.5-2(m, 6H); 2.13 (dd, J=11.5 Hz, J'=1.5 Hz, 1H); 3.74 (t, J=7.8 Hz, 1H); 3.85 (bd, J=7.1 Hz, 1H); 3.90 (t, J=8.0 Hz, 1H); 4.12 (dd, J=9.7 Hz, J'=2.8 Hz, 1H); 4.25 (t, J 7.9 Hz, 1H); 7.4 (m, 5H)

$^{13}$C NMR δ: ppm 19.3; 28.0; 30.0; 47.4; 63.9; 73.0; 89.9; 116; 128.2; 128.6; 129.0; 137.4

Stage III (1R,4R,9aS)-1-amino-4-phenyloctahydropyrido[2,1-c][1,4]oxazine

A reactor under a nitrogen atmosphere is charged with 2 g (0.0088 mol) of (3R,5S,8aR)-3-phenyl-5-cyanooxazolidino[3,2-a]piperidine and 150 cm$^3$ of distilled hexane. The mixture is stirred at 20° C. until dissolution has taken place, and 27 cm$^3$ (0.027 mol) of a 1M solution of diisobutylaluminum hydride in hexane are then added slowly.

The reaction medium is stirred for 4 hours at 20° C. and then hydrolyzed with 15% aqueous sodium hydroxide solution until a white precipitate has formed.

The solid phase is extracted several times in the heated state with methylene chloride.

The combined methylene chloride phases are dried over magnesium sulfate and then concentrated under reduced pressure. The colorless oil obtained is purified by chromatography on a silica column.

1.1 g (54%) of (1R,4R,9aS)-1-amino-4-phenyloctahydropyrido[2,1-c][1,4]oxazine are thereby obtained in the form of white crystals.

$^1$H NMR 400 MHz (CDCl$_3$)δ: ppm

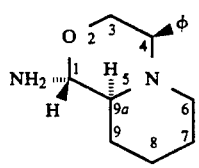

1.3; 1.8; 2.0 3 multiplets, piperidine 2.7; triplet of doublets, H$_6$ equatorial 3.25; 3.55; 3.70 doublet of doublets, triplet, doublet of doublets, H$_3$, H$_4$ 4.00 doublet, H$_1$ 7.1; 7.3 multiplet, phenyl $^{13}$C NMR (CDCl$_3$) δ: ppm 24.6; 25.5; 28.5; 52.5 (CH$_2$) 67.4; 67.7; 86.5 (CH) 71.5 (CH$_2$) 126.6; 127.9; 128.6 (CH) 130.2 (Cq)

Stage IV

N-[(1R,4R,9aS)-4-phenyloctahydropyrido[2,1-c][1,4]oxazin-1-yl]-3,4,5- trimethoxybenzamide A reactor under a nitrogen atmosphere is charged with 1.4 g(0.006 mol) of 3,4,5-trimethoxybenzoyl chloride and 20 cm$^3$ of dichloromethane, and a previously prepared solution of 1.1 g (0.0047 mol) of (1R,4R,9aS)-1-amino-4-phenyloctahydropyrido[2,1-c][1,4]oxazine in 20 cm$^3$ of dichloromethane is then added.

3 cm$^3$ of 15% aqueous sodium hydroxide solution are then added and the mixture is thereafter stirred for 3 hours at 20° C.

After addition of water, extraction with dichloromethane, drying of the methylene chloride phases over magnesium sulfate and concentration under reduced pressure, 2.3 g of crude product are obtained, which product is purified by flash chromatography on a silica column; eluant—50:50 hexane/diethyl ether.

1.3 g (65%) of N-(4-phenyloctahydropyrido[2,1-c](1,4]oxazin-1-yl)-3,4,5-trimethoxybenzamide are thereby obtained in the form of white crystals.

Melting point: 126°-128° C. (melting point of the hydrochloride: 270°-280° C.)

Optical rotation: $[\alpha]_D^{20} = -58,9°$ (CHCl$_3$, C = 0,47)

$^1$H NMR (CDCl$_3$) δ=ppm

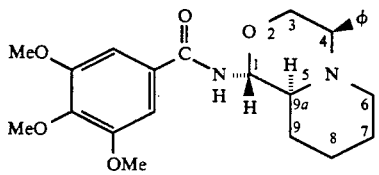

0.9; 1.3; 1.5; 1.9 4 multiplets, piperidine 2.38 triplet, H9a, axial 2.80 doublet, H6 equatorial 3.4; 3.75; 3.8 doublet of doublets, triplet, doublet of doublets, H3, H4 3.85 broad singlet, 3×(OMe) 5.50 triplet, H1 7.1 singlet; 7.3 broad singlet Aromatic rings $^{13}$C NMR (CDCl3) δ: ppm 24.4; 25.3; 27.3; 52.5 (CH2) 56.2; 60.7 (CH3) 65.0; 67.2; 81.1 (CH) 72.1 (CH2) 104.9; 127.6; 127.9; 128.6 (CH) 136.6; 153.1; 166.7 (Cq)

Microanalysis:
calculated: C(67.58), H(7.10), N(6.57);
Measured: C(67.71), H(6.97), N(6.29);

EXAMPLE 2

N-[(1R,4R,9aS)-4-ethyloctahydropyrido[2,1-c][1,4]oxazin-1-yl]-3-4-5-trimethoxybenzamide Using the procedure described in Example 1, but replacing 2-amino-2-phenylethanol by (−)-(R)-2-aminobutanol, N-[(1R,4R,9aS)-4-ethyloctahydropyrido[2,1-c)[1,4]oxazin-1-yl]-34-5-trimethoxybenzamide is obtained.

Melting point: 180° C.

Optical rotation: $[\alpha]_D^{20}$ = −67,2° (MeOH, C = 6,7 mg/ml)

$^1$H NMR (CDCL3) δ: ppm

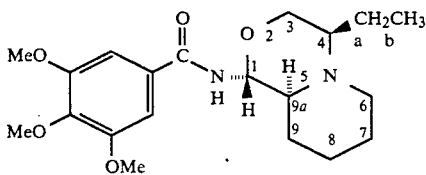

0,85; triplet; 3H; CH3b 1,3; 1,6; 1,8; multiplets; piperidine and CH2a 2,05; triplet H9a 2,2; multiplet; H4 3,35; doublet; H6 équatorial 3,6; triplet; H3a 3,8; multiplet 10H; 3 méthoxy and H3 équatorial 5,3 triplets H1 6,7 doublet NH 7,0; 2H; aromatic ring $^{13}$C NMR (CDCl3) δ: ppm 10,2 (CH3) 21,8; 24,4; 25,9; 27,7; 51 (CH2) 56,8; 61,3 (CH3O) 61,8; 65,9 (CH) 70,2 (CH2) 81 (CH) 105 (Cq) 129,5 (CH aromatic) 153,6 (Cq aromatic) 167 (C=O)

EXAMPLES 3 TO 6

Using the same procedure as that described in Example 1, but replacing phenylglycine in stage I by:
(L)-phenylalanin, N-(4-benzyloctahydropyrido[2,1-c](1,4]oxazin-1-yl)-3,4,5-trimethoxybenzamide is obtained.

Melting point: 214 ° C.

Optical rotation: $[\alpha]_D^{20}$ = −49,2° (CHCl3, C = 7,1 mg/ml)

$^1$H NMR (CDCL3) δ: ppm

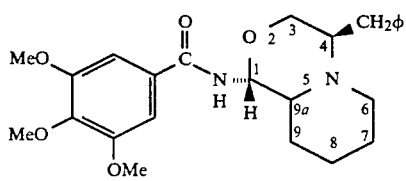

1,1; 1,3; 1,6; 1,75; 4 multiplets; piperidine 1,95; ; triplet of doublet; H6 axial 2,05; triplet H9a 2,35; doublet of doublets; 1H; benzylic CH2 2,62; multiplet; R4 3,2; doublet of doublets; 1H; benzylic CH2 3,5; broad doublet; 2H; H6 equatorial axial H3 3,65; doublet of doublets; H3 equatorial 3,8; 9H; méthoxy 5,3; triplet; H1 6,85; doublet; NH 7; singulet; 2H aromatic 7,25; multiplet; 5H aromatic $^{13}$C NMR (CDCl3) δ: ppm 23,7; 26,5; 27,2; 35,6; 51,1 (CH2) 56,2; 58 (OCH3) 61,9; 65,7 (CH) 70 (CH2) 86 (CH) 104 (Cq) 126,5; 128,6; 128,7; 129; 138,3; (CH aromatic) 153,1 (Cq aromatic) 166 (CO)

(L)-homophenylalanine, N-(4-phenethyloctahydropyrido[2,1-c][1,4]oxazin-1-yl)-3,4,5-trimethoxybenzamide is obtained.

(L)-leucine, N-[4-(isopropylmethyl)octahydropyrido[2,1-c][1,4]oxazin-1-yl]-3,4,5-trimethoxybenzamide is obtained.

3-cyclohexyl-2-aminopropanoic acid, N-[4-(cyclohexylmethyl)octahydropyrido[2,1-c][1,4]oxazin-1-yl]-3,4,5-trimethoxybenzamide is obtained.

EXAMPLE 7

N-[(1R,4R,9aS)-4-phenyloctahydropyrido[2,1-c)][1,4]oxazin-1-yl]-2,6- dimethoxy-3,5-dibromo benzamide Using the procedure described in Example 1, but replacing 3,4,5-trimethoxybenzoyl chloride in stage IV by 2,6-dimethoxy-3,5-dibromobenzoyl chloride, N-[(1R,4R,9aS)-4-phenyloctahydropyrido[2,1-c][1,4]oxazin- 1-yl]-2,6-dimethoxy-3,5-dibromobenzamide is obtained.

Optical rotation: $[\alpha]_D^{20}$ = −59,5° (CHCl3, C = 0,38)

$^1$H NMR (CDCl3) δ: ppm

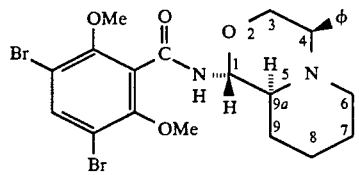

1.3–1.9; multiplet 7H, piperidine 2.0; triplet of doublets, H9a axial 2.70; broad doublet, H6 equatorial 3.25; 3.70; 3.80 doublet of doublets, doublet of doublets, triplet, H3, H4 3.85 singlet, 6H, 2×(OCH3) 5.3 triplet, H1 6.2 doublet, NH—CO 7.3 multiplet 5H, aromatic 7.8 singlet 1H, aromatic $^{13}$C NMR (CDCl3) δ: ppm 24.4; 25.4; 26.9; 52.4; 72.1 (CH2) 62.7 (—OMe)2 65.2; 67.2; 80.3 (CH) 113.0; 127.8; 128.2; 128.6; 137.3 (aromatic CH) 139.1; 155.0; 164.0 (Cq)

Microanalysis: Calculated: C(49.84), H(4.73), N(5.05); Measured: C(49.70), H(4.82), N(5.08).

EXAMPLE 8

N-[(1R,4R,9aS)-4-ethyloctahydropyrido[2,1-c](1,4]oxazin-1-yl]-3,4,-dichlorobenzamide Using the same procedure as that described in Example 2, but replacing 3,4,5-trimethoxybenzoyl chloride by 3,4-dichlorobenzoyl chloride, N-[(1R,4R,9aS)-4-ethyloctahydropyrido[2,1-c][1,4]oxazin-1-yl)-3,4-dichlorobenzamide is obtained Melting point: 214° C.

EXAMPLES 9 TO 14

Using the same procedure as that described in Example 1, but replacing 3,4,5-trimethoxybenzoyl chloride in stage IV by benzoyl chloride, N-[(1R,4R,9aS)-4-phenyloctahydropyrido[2,1-c][1,4]oxazin-1-yl]benzamide is obtained Melting point of the hydrochloride: 210°–220° C.

2,3-dichlorobenzoyl chloride, N-[(1R,4R,9aS)-4-phenyloctahydropyrido[2,1-c][1,4]oxazin-1-yl]-3,4-dichlorobenzamide is obtained Melting point of the hydrochloride: 220°–225° C.

4-methoxybenzoyl chloride, N-[(1R,4R,9aS)-4-phenyloctahydropyrido[2,1-c][1,4]oxazin-1-yl]-4-methoxybenzamide is obtained Melting point: 242° C.

Optical rotation: $[\alpha]_D^{20} = -61,5°$ (CHCl$_3$, 10 mg/ml)

2-methoxy-4-amino-5-chlorobenzoyl chloride, N-[(1R,4R,9aS)-4-phenyloctahydropyrido[2,1-c][1,4]oxazin-1-yl]-2-methoxy-4-amino-5-chlorobenzamide is obtained Melting point: 200°–204° C.

Optical rotation: $[\alpha]_D^{20} = -46,6°$ (CHCl$_3$, 10 mg/ml)

3,4-dimethoxybenzoyl chloride, N-[(1R,4R,9aS)-4-phenyloctahydropyrido[2,1-c][14]oxazin-1-yl]-3,4-dimethoxybenzamide is obtained Melting point: 160° C.

Optical rotation: $[\alpha]_D^{20} = -55,9°$ (CHCl$_3$, 10 mg/ml)

4-(trifluoromethyl)benzoyl chloride, N-[(1R,4R,9aS)-4-phenyloctahydropyrido[2,1-c][1,4]oxazin-1-yl]-4-(trifluoromethyl)benzamide is obtained.

Melting point: >270° C.

Optical rotation: $[\alpha]_D^{20} = -59,5°$ (CHCl$_3$, 10 mg/ml)

EXAMPLE 15

N-[(1S,4S,9aR)-4-phenyloctahydropyrido[2,1-c][1,4]oxazin-1-yl]-3,4,5-trimethoxybenzamide Using the procedure described in Example 1, but replacing (−)-(2R)-2-phenylglycine in stage I by (+)-(2S)-2-phenylglycine, N-[(1S,4S,9aR)-4-phenyloctahydropyrido[2,1-c)][1,4]oxazin-1-yl]-3,4,5-trimethoxybenzamide is obtained.

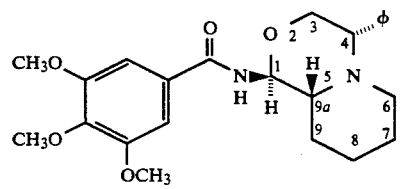

Optical rotation: $[\alpha]_D^{20} = +56,7°$ (CHCl$_3$, C = 0,58)

Melting point of the hydrochloride: 195°–200° C.

EXAMPLE 16

N-[(1S3S,4R,9aS)-4-methyl-3-phenyloctahydropyrido[2,1-c][1,4]oxazin-1-yl]-3,4,5-trimethoxybenzamide

Stage I 3S,4R)-1-amino-3-phenyl-4-methyloctahydropyrido[2,1-c][1,4]oxazine

This compound is prepared from (2S,3R,5S,8aR)-2-phenyl-3-methyl-5-cyanooxazolidino[3,2-a]piperidine by reduction with diisobutylaluminum hydride as in stage III of Example 1.

(3S,4R)-1-Amino-3-phenyl-4-methyloctahydropyrido[2,1-c][1,4]oxazine is obtained in the form of a mixture of two epimers, which is employed as it is in the next stage of the synthesis.

Stage II

N-[1R,3S,4R,9aS)-4-methyl-3-phenyloctahydropyrido[2,1-c][1,4]oxazin-1-yl]-3,4,5-trimethoxybenzamide (3S,4R)-1-Amino-3-phenyl-4-methyloctahydropyrido[2,1-c][1,4]oxazine is treated with 3,4,5-trimethoxybenzoyl chloride as in stage IV of Example 1.

A mixture of epimers is obtained, which epimers are separated by flash chromatography on a silica column (eluant—CH$_2$Cl$_2$ 98%, CH$_3$OH 2%)

The preponderant isomer (75%) is N-[(1R,3S,4R,9aS)-4-methyl-3-phenyloctahydropyrido[2,1-c][1,4]oxazin-1-yl]-3,4,5-trimethoxybenzamide.

Melting point: 114° C.

Optical rotation: $[\alpha]_D^{20} = -6°$ (CHCl$_3$, C = 0,45)

$^1$H NMR (CDCl$_3$) δ: ppm

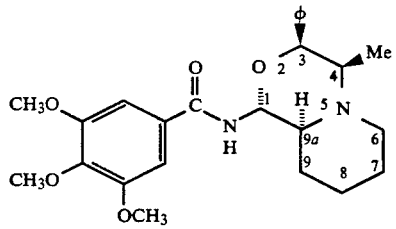

0.80; 3H; CH$_3$ at C$_4$, doublet 1.15–1.60; 6H, piperidine 1.80; 1H, H$_6$ axial, triplet of doublets 2.60; 1H, H$_4$, multiplet 2.80; 1H, H$_{9a}$, quartet of doublets 2.90; 1H, H$_6$ equatorial, doublet of multiplets 5.2; 1H, H$_3$, doublet 6.6; 1H, H$_1$ 7.3–7.6 aromatic protons $^{13}$NMR (CDCl$_3$) δ: ppm 15.7 (C$_{10}$) 23.7; 25.9; 28.6; 52.6 (CH$_2$) 56.4; 60.9 (—OCH$_3$) 59.6; 60.2 (CH) 75.6; 95.2 (CH) 107.3; 127.5; 128.0 (aromatic CH) 137.7; 152.9; 165.0 (aromatic Cq)

Microanalysis: Calculated: C(68.16), H(7.32), N(6.36); Measured: C(68.20), H(7.16), N(6.43).

EXAMPLE 17

N-[(1R,4R)-1-methyl-4-phenyloctahydropyrido[2,1-c][1,4]oxazin-1-yl]-3,4,5- trimethoxybenzamide

Stage I (1R,4R)-1-amino-1-methyl-4-phenyloctahydropyrido[2,1-c][1,4]oxazine

In a reactor under a nitrogen atmosphere, 11.6 cm³ (0.0185 mol) of methyllithium (dissolved in ether) are added to a solution of 3.85 g (0.0168 mol) of (3R,5S,8aR)-3-phenyl-5-cyanooxazolidino[3,2-a]piperidine in 50 cm³ of anhydrous ether at −5° C.

The mixture is stirred for 2 h 30 min at 20° C. and then diluted with aqueous ammonium chloride solution, and the aqueous phase is extracted with methylene chloride.

After drying and removal of the solvent, 3.8 g of a yellow oil are obtained, which oil is redissolved directly in 40 cm³ of methanol and then diluted with 40 cm³ of THF.

The reaction medium is brought to pH3 by adding 1N HCl and then maintained at this pH after the addition of 1.16 g of sodium cyanoborohydride.

After 90 minutes of stirring under reflux, the medium is diluted with saturated aqueous ammonium chloride solution and extracted with methylene chloride.

The crude product is purified by chromatography on a silica column (eluant : ethyl ether).

2.4 g (60%) of (1R,4R)-1-amino-1-methyl-4-phenyloctahydropyrido[2,1-c][1,4]oxazine are obtained.

Optical rotation: $[\alpha]_D^{20} = -99,9°$ (CHCl₃, C = 0,46)

¹H NMR (CDCl₃) δ: ppm

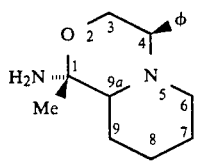

1.2-2.2 multiplets, 7H, piperidine 1.35; singlet, 3H, —CH₃ 2.1; broad singlet, 2H, —NH₂ 2.2; doublet of doublets, H₉ₐ 2.75; triplet of doublets, H₆ equatorial 3.2; 3.5; 2 doublets of doublets, H₄ and H₃ equatorial 3.8; triplet, H₃ axial 14 7.2-7.4; multiplet, 5H, aromatic ¹³C NMR (CDCl₃) δ: ppm 24.6; 25.4; 27.6; 53.5; 65.4 (CH₂) 26.5 (CH₃) 68.5; 69.1 (CH) 84.5 (Cq) 127.5; 127.9; 128.5; 140.0 (aromatic)

Stage II

N-[(1R,4R)-1-methyl-4-phenyloctahydropyrido[2,1-c][1,4]oxazin-1-yl]-3,4,5-trimethoxybenzamide Using the procedure described in stage IV of Example 1, but replacing (1R,4R,9aS)-1-amino-4-phenyloctahydropyrido[2,1-c][1,4]oxazine by (1R,4R)-1-amino-1- methyl-4-phenyloctahydropyrido[2,1-c][1,4]oxazine, N- [(1R,4R)-1-methyl-4-phenyloctahydropyrido[2,1-c][1,4]oxazin-1-yl]-3,4,5-trimethoxybenzamide is obtained.

Optical rotation: $[\alpha]_D^{20} = -47,8°$ (CHCl₃, C = 4,3)

Melting point of the hydrochloride: >200° C.

¹H NMR (CDCl₃) δ: ppm

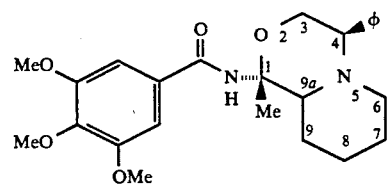

1.3-2.0; multiplets; 7H; piperidine 1.8; singlet; 3H; -CH₃ 2.3; doublet of doublets; H₉ₐ 2.8; triplet of doublets; H₆ equatorial 3.35; 3.6; doublet of doublets; doublet of doublets; H₄ and H₃ equatorial 3.7; triplet; H₃ axial 3.9; 3.95; 2 singlets; 9H; —(OCH₃)₃ 7.2; 7.35; 2 singlets; 7H; aromatic ¹³C NMR (CDCl₃) δ: ppm 24.1; 25.5; 27.1; 52.8; 66.4 (CH₂) 56.3; 60.9 —(OCH₃) 68.6; 69.4 (CH) 84.0 (Cq) 104.5; 127.6; 127.9; 128.5; 138.9; 153.3 (aromatic) 166.2 (NHCO)

EXAMPLE 18

N-[(1R,4R,9aS)-4-phenyloctahydropyrido[2,1-c][1,4]oxazin-1-yl]-2-furancarboxamide Using the same procedure as that described in Example 1, but replacing 3,4,5-trimethoxybenzoyl chloride in stage IV by 2-furancarbonyl chloride, N-[(1R,4R,9aS)-4-phenyloctahydropyrido[2,1-c][1,4]oxazin-1-yl]-2-furancarboxamide is obtained in a 79% yield.

Melting point of the hydrochloride: 240° C.

Optical rotation: $[\alpha]_D^{20} = -70°$ (CHCl₃, 9 mg/ml)

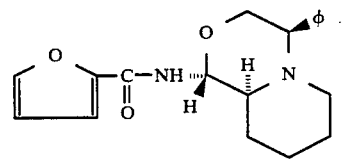

EXAMPLE 19

N-[(1R,4R,9aS)-4-phenyloctahydropyrido[2,1-c][1,4]oxazin-1-yl]-2-indolecarboxamide Using the same procedure as that described in Example 1, but replacing 3,4,5-trimethoxybenzoyl chloride in stage IV by 2-indolecarbonyl chloride, N-[(1R,4R,9aS)-4-phenyloctahydro pyrido[2,1-c][1,4]oxazin-1-yl]-2-indolecarboxamide is obtained.

¹H NMR (CDCl₃) δ: ppm

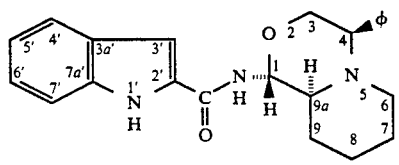

1-2; unresolved peaks; 6H 2.18; doublet of triplets; H₆ axial 2.75; broad doublet; H₆ equatorial 3.3; doublet of doublets; H₄ 3.6–3.82; multiplet; 2H; CH₂ (3) 5.40; triplet; H₁ 6.58; broad doublet; 1H; NHCO 6.97; doublet; H₅ 7.2–7.5; unresolved peaks; 8H aromatic 7.68; doublet; H₈ 9.25; broad singlet; NH₁′

¹³C NMR (CDCl₃) δ: ppm 24.3; 25.37; 27.47: C₇; C₈; C₉ 52.44: C₆ 61.35; 65.10: C₉ₐ; C₄ 71.83: C₃ 80.51: C₁ 103.42;112.10;120.74;122.19;124.87: C₃′; C₅′; C₆′; C₇; C₈′ 127.79; 128.13; 128.59 : C aromatic

EXAMPLES 20 TO 26

Using the same procedure as that described in Example 1, but replacing 3,4,5-trimethoxybenzoyl chloride in stage IV by:

2,5dimethoxycinnamoyl chloride, N-[(1R,4R,9aS)-4-phenyloctaropyrido[2,1-c][1,4]oxazin-1-yl]-2,5-dimethoxy cinnamide.

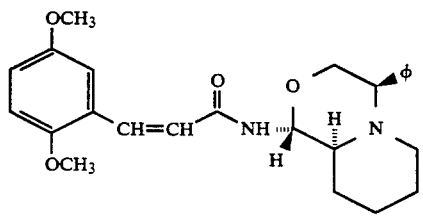

is obtained.

2-thiophenecarbonyl chloride, N-[(1R,4R,9aS)-4-phenyloctahydropyrido[2,1-c][1,4]oxazin-1-yl]-2-thiophene carboxamide:

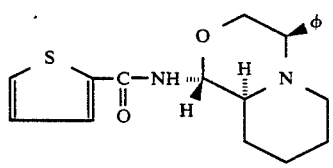

is obtained.

2-naphthoyl chloride, N-[(1R,4R,9aS)-4-phenyloctahydropyrido[2,1-c][1,4]oxazin-1-yl]-2-naphthamide:

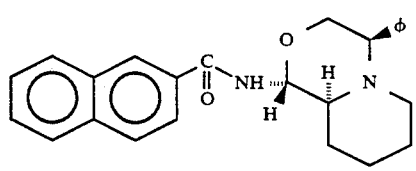

is obtained.

nicotonoyl chloride, N-[(1R,4R,9aS)-4-phenyloctahydropyrido[2,1-c][1,4]oxazin-1-yl]-nicotinamide:

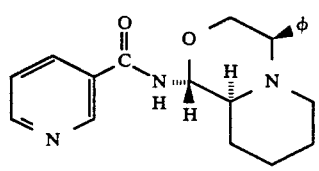

is obtained.

2-benzofurancarbonyl chloride, N-[(4-phenyloctahydropyrido[2,1-c][1,4]oxazin-1-yl)-2-benzofurancarboxamide:

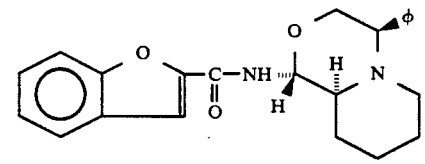

is obtained.

quinaldoyl chloride, N-[(4-phenyloctahydropyrido[2,1-c][1,4]oxazin-1-yl)-2-quinolinecarboxamide:

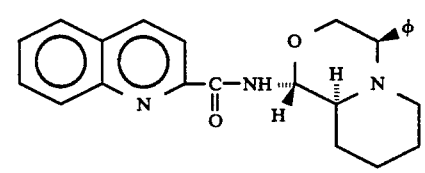

is obtained.

3-quinolinecarbonyl chloride, N-[(4-phenyloctahydropyrido[2,1-c][1,4]oxazin-1-yl)-3-quinolinecarboxamide:

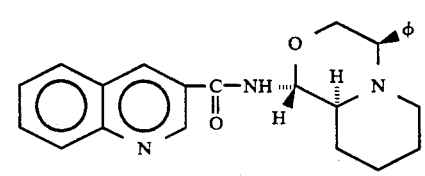

is obtained.

EXAMPLES 27 TO 28

In the same manner, the following are also obtained:
N-(4-phenyloctahydropyrido[2,1-c][1,4]oxazin-1-yl)acetamide
N-(4-phenyloctahydropyrido[2,1-c][1,4]oxazin-1-yl)-3-isoquinolinecarboxamide

EXAMPLE 29

N-(perhydropyrido[2,1-c][1,4]benzoxazin-6-yl)-3,4,5-trimethoxybenzamide

Using the procedure described in Example 1, but replacing 2-amino-2-phenylethanol in stage II by 2-aminocyclohexanol, N-(perhydropyrido[2,1-c][1,4]benzoxazin-6-yl)-3,4,5-trimethoxybenzamide is obtained.

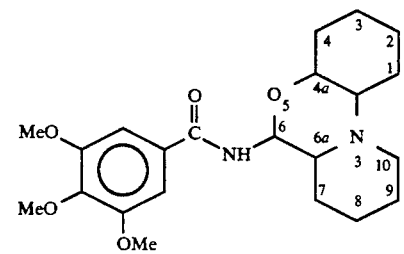

EXAMPLE 30

Using the same procedure as that described in Example 1, but replacing 3,4,5-trimethoxybenzoyl chloride by 3,4-dichlorobenzoyl chloride, N-[(1R, 4R, 9aS) -4- ethyloctahydropyrido [2,1-c][1,4] oxazin-1-yl] 3,4-dichloro benzamide is obtained Melting point: 214° C.

Optical rotation: $[\alpha]_D^{20} = -57,2°$ (MeOH, C = 5,5 mg/ml)

$^1$H MNR (CDCL$_3$) δ: ppm

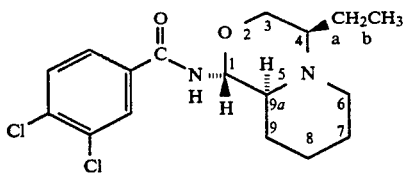

0,85; triplet; 3H; CH$_3$b 1,3; 1,6; 1,8; multiplets; piperidine and CH2a 1,95 triplet H$_{9a}$ 2,15; multiplet H$_4$ 3,2; doublet; H$_6$ eq 3,6; triplet; H$_{3a}$ 3,8; doublet of doublets H$_3$ eq 5,2 triplet H$_1$ 6,5 doublet NH 7,45; 7,6 doublet of doublets; aromatic 7,85; singulet; 1H aromatic $^{13}$C MNR (CDCl$_3$) δ: ppm 10 (CH$_3$) 21,7; 24,2; 25,8; 27,6; 50,8 (CH$_2$) 61,5; 65,6 (CH) 69,9 (CH$_2$) 88,3 (CH) 105 (Cq) 126,6; 129,7; 131 (CH aromatic) 165,3 (C=O)

EXAMPLE 31

Tablets Containing 25 mg of N-[(1R,4R,9aS)-4-phenyloctahydropyrido[2,1-c][1,4]oxazin-1-yl]-3,4,5-trimethoxybenzamide

| Preparation formula for 1000 tablets | |
| --- | --- |
| N-[(1R,4R,9aS)-4-Phenyloctahydropyrido[2,1-c][1,4]oxazin-1-yl]-3,4,5-trimethoxybenzamide | 25 g |
| Wheat starch | 20 g |
| Maize starch | 20 g |
| Lactose | 60 g |
| Magnesium stearate | 1 g |
| Silica | 1 g |
| Hydroxypropylcellulose | 2 g |

EXAMPLE 32

Pharmacological Study of the Compounds of the Invention

A. Antagonism of Apomorphine-Induced Hypothermia

This test is based on the ability possessed by some psychotropic compounds to antagonize an apomorphine- induced hypothermia (Puech et al., Psychopharmacology (1981) 75 p 84–91).

Mice randomized in groups of 6 receive a subcutaneous injection of 1 mg/kg of apomorphine, producing a marked hypothermia which is measured 30 minutes after injection.

The test products are injected intraperitoneally 30 minutes before the injection of apomorphine, and the temperature of the animals is measured 30 minutes after the injection of apomorphine.

The compounds of the invention very significantly antagonize the hypothermia induced by 1 mg/kg of apomorphine, testifying to a psychotropic activity.

These compounds do not inhibit either the hypothermia induced by 16 mg/kg of apomorphine, or the stereotyped behavior and climbing induced by 1 mg/kg of apomorphine.

B. Demonstration of Psychotropic Activity According to the Technique Known as the Tail Suspension Test This test is based on observation of the behavior of mice suspended by the tail.

Mice randomized in groups of 6 are suspended by the tail for 6 minutes. The movements and the episodes of immobility are recorded automatically using an apparatus which enables the period of immobility and also the strength of the movements to be determined according to a technique developed by Steru et al., J. Pharmacol. (1986) 17 348–350 and Prog. Neuro. Psychopharmacol. Biol. Psychiatry (1987) 11 659–671.

The compounds of the invention, such as, for example, N-[(1R,4R,9aS)-4-phenyloctahydropyrido[2,1-c][1,4]oxazin-1-yl]-3,4,5-trimethoxybenzamide, greatly increase the period of immobility, testifying to a "neuroleptic type" activity.

C. Antagonism of the Hyperactivity Induced in Rats by D-amphetamine or methylphenidate This test is based on the ability possessed by some compounds to inhibit the hyperactivity induced in rats by 1. 5 mg/kg of amphetamine or 10 mg/kg of methylphenidate.

Sprague-Dawley rats weighing f rom 200 to 250 g receive the test compounds IP 30 minutes before the administration of 1.5 mg/kg of amphetamine or 10 mg/kg of methylphenidate.

The locomotor activity of these rats is then measured during the four hours following the administration of amphetamine or methylphenidate.

The compounds of the invention very significantly inhibit the hyperactivity induced by D-amphetamine and by methylphenidate, suggesting that they possess antidopaminergicactivity at central level.

We claim:

1. A compound selected from 1-acylaminooctahydropyrido[2,1-][1,4]oxazines of formula (I):

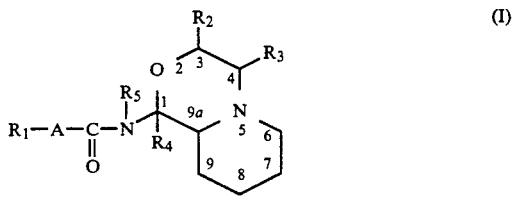

in which:
R$_1$ represents hydrogen or an optionally-substituted mono- or bicyclic system chosen form phenyl, naphthyl, pyridyl, thienyl, furyl, quinolyl, isoquinolyl, indolyl, indolinyl, perhydroindolyl, and benzofuryl, A represents a σ bond or a saturated or unsaturated, linear or branched alkylene having 1 to 4 carbon atoms inclusive, with the reservation that, when R$_1$ represents hydrogen, A cannot represent a σ bond, R$_2$ and R$_3$ each represent, independently of one another:
hydrogen,
linear or branched and optionally-substituted alkyl having 1 to 6 carbon atoms inclusive,
a group —(CH$_2$)$_n$B, n being 0, 1, 2, or 3 and B representing a C$_5$-C$_7$ cycloalkyl or phenyl monocyclic system, substituted or unsubstituted, R4 and R5 each represent, independently of one another, hydrogen, linear or branched alkyl having 1 to 4 carbon atoms inclusive or a group —(CH2)$_n$B as above defined, the term substituted associated with the expression "monocyclic system" means that the system may be substituted with 3 or 4 lower-alkoxy having 1 to 4 carbon atoms inclusive branched or linear or 2 lower-alkoxy plus 2 halogen atoms SO2R6, the substituents being identical or different, wherein the term associated with the expression alkyl means that this group may be substituted wit one or more linear or branched lower-alkoxy having 1 to 4 carbon atoms inclusive, its isomers, diastereoisomers and enantiomers, isolated or in the form of a mixture, and its addition salts with a pharmaceutically-acceptable inorganic or organic acid.

2. A compound as claim in claim 1 which is selected from N-(4-phenyloctahydropyrido[2,1-c][1,4]oxazin-1-yl]-3,4,5-trimethoxybenzamide, its isomers and addition salts thereof with a pharmaceutically-acceptable inorganic or organic acid.

3. A compound as claimed in claim 1 or 2, which is selected from N-[(1R,4R,9aS)-4-phenyloctahydropyrido[2,1-c][1,4]oxazin-1-yl]-3,4,5-trimethoxybenzamide, the formula of which is shown below, and also its addition salts with a pharmaceutically-acceptable inorganic or organic acid,

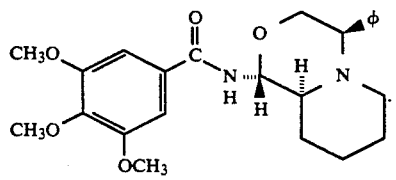

4. A compound as claimed in claim 1, which is selected from N-[(1R,4R,9aS)-4-phenyloctahydropyrido[2,1-c][1,4]oxazin-1-yl]-2,6-dimethoxy-3,5-dibromobenzamide, its isomers and their addition salts thereof with a pharmaceutically-acceptable inorganic or organic acid.

5. A compound as claimed in claim 1, which is selected from N-[(1-methyl-4-phenyloctahydropyrido[2,1- c][1,4]oxazin-1-yl]-3,4,5-trimethoxybenzamide, its isomers and addition salts thereof with a pharmaceutically-acceptable inorganic or organic acid.

6. A compound as claimed in claim 1, which is selected from N-(4-methyl-3-phenyloctahydropyrido[2,1-c][1,4]oxazin-1-yl]-3,4,5-trimethoxybenzamide, its isomers and addition salts thereof with a pharmaceutically-acceptable inorganic or organic acid.

7. A compound as claimed in claim 1, which is selected from N-[(1S, 4S, 9aS)-4-phenyloctahydropyrido[2,1- c][1,4]oxazin-1-yl]-3,4,5-trimethoxybenzamide, its isomers, and addition salts thereof with a pharmaceutically-acceptable inorganic or organic acid.

8. A compound as claimed in claim 1, which is selected from N-[(1R,4R)-1-methyl-4-phenyl-octahydropyrido[2,1- c][1,4]oxazin-1-yl]-3,4,5-trimethoxybenzamide, its isomers, and addition salts thereof with a pharmaceutically-acceptable inorganic or organic acid.

9. A method for treating a living animal or human afflicted with a psycho-behavioral disorder selected from depressive states and psychosis, comprising the step of administering to the said living animal or human an amount of a compound of claim 1 which is effective for alleviation of said condition.

10. A pharmaceutical composition useful for the treatment of psycho-behavioral disorders, containing as active principle an effective amount of a compound as claimed in claim 1, in combination with a pharmaceutically-acceptable excipient or vehicle.

* * * * *

UNITED STATES PATENT AND TRADEMARK OFFICE
CERTIFICATE OF CORRECTION

PATENT NO. : 5,310,739

DATED : May 10, 1994

INVENTOR(S) : Henri P. Husson, Jean C. Quirion, Martine Bonin, Béatrice Guardiola, Gérard Adam, Pierre Renard It is certified that error appears in the above-indentified patent and that said Letters Patent is hereby corrected as shown below:

Column 1 line 5; "The invention" should read -- The present invention --.
Column 1, approximately line 40, "a bond" should read -- a σ bond --.
Column 2, line 35; delete "10".
Column 4, line 50; "c)" should read -- c] --.
Column 5, line 53; "J 7.9" should read --J=7.9--.
Column 6, line 51; "(1,4]" should read --[1,4] --.
Column 7, line 19; "[2,1-c)" should read --[2,1-c]--.
Column 7, line 19; "-34-5-" should read -- 3-4-5- --.
Column 7, line 50; "(1,4]" should read -- [1,4] --.
Column 8, line 1; "$R_4$" should read -- $H_4$ --.
Column 9, line 32; "[14]" should read -- [1,4] --.
Column 10, line 3; "(1S3S," should read -- [(1S,3S,--.
Column 10, line 24; "N-[1R," should read -- N- [(1R, --.
Column 10, line 62; "$^{13}$NMR" should read -- $^{13}$C NMR --.
Column 11, line 53; "axial 14 7.2" should read -- axial 7.2 --.
Column 12, approximately line 23; "($CH_2$) 56.3;" should read -- ($CH_2$ 23.1 ($CH_3$) 56.3; --
Column 13, approximately line 14; "2,5dimethoxycinnamoyl" should read -- 2,5-dimethoxycinnamoyl --.
Column 13, approximately line 15; "phenyloctaropyrido" should read -- phenyloctahydropyrido --.
Column 13, line 66; "N-[(4-" should read -- N-(4- --.
Column 14, line 11; "N-[(4-" should read -- N-(4- --.
Column 14, line 23; "N-[(4-" should read -- N-(4- --.
Column 16, line 26; "f rom" should read -- from --.
Column 16, line 39; "[2,1-]" should read -- [2,1-c]--.
Column 17, line 7; "defined, the" should read -- defined, wherein the --.
Column 17, line 7; "substituted" should read --"substituted"--.

UNITED STATES PATENT AND TRADEMARK OFFICE
CERTIFICATE OF CORRECTION

PATENT NO. : 5,310,739
DATED : May 10, 1994
INVENTOR(S) : Henri P. Husson, et al It is certified that error appears in the above-indentified patent and that said Letters Patent is hereby corrected as shown below:

Column 17, line 7; "defined, the" should read -- defined, wherein the --.

Column 17, approximately line 18; "term associated" should read -- term "substituted" associated
Column 17, line 18; "alkyl" should read -- "alkyl" --.
Column 17, line 20; "wit" should read -- with --.
Column 17, appoximately line 35; "yl]" should read --yl)--.

Column 18, approximately line 13; "and their addition" should read --and addition--
Column 18, approximately line 17; "N-[(1-methyl" should read -- N-(1-methyl--. (Cl. 5)
Column 18, line 18; "-1-yl]" should read -- -1-yl)--.
Column 18, line 23; "-1-yl]" should read -- 1-yl)--.
Column 18, approximately line 27; "9aS) should read --9aR)--.

Signed and Sealed this

Eleventh Day of October, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,310,739
DATED : May 10, 1994
INVENTOR(S) : Henri P. Husson, Jean C. Quirion, Martine Bonin, Béatrice Guardiola, Gérard Adam and Pierre Renard It is certified that error appears in the above-indentified patent and that said Letters Patent is hereby corrected as shown below:

Column 17, approximately line 12; "inclusive" should read -- inclusive, --

Column 17, approximately line 15; delete "$SO_2R_6$".

Column 17, last line; "acid," should read -- acid. --

Signed and Sealed this

Twenty-second Day of August, 1995

Attest:

BRUCE LEHMAN

*Attesting Officer*  *Commissioner of Patents and Trademarks*